United States Patent [19]

Krause et al.

[11] Patent Number: 5,130,440
[45] Date of Patent: Jul. 14, 1992

[54] PROCESS FOR THE PRODUCTION OF 2-ALKYL- OR ALKENYL-2-OXAZOLINES

[75] Inventors: Horst-Juergen Krause; Peter Neumann, both of Duesseldorf, Fed. Rep. of Germany

[73] Assignee: Henkel Kommanditgesellschaft auf Aktien, Duesseldorf, Fed. Rep. of Germany

[21] Appl. No.: 673,250

[22] Filed: Mar. 20, 1991

Related U.S. Application Data

[63] Continuation of Ser. No. 481,744, Feb. 14, 1990, abandoned, which is a continuation of Ser. No. 269,271, Nov. 9, 1988, abandoned.

[30] Foreign Application Priority Data

Nov. 10, 1987 [DE] Fed. Rep. of Germany ....... 3738197
Jul. 22, 1988 [DE] Fed. Rep. of Germany ....... 3824982

[51] Int. Cl.$^5$ .............................................. C07D 263/12
[52] U.S. Cl. ................................. 548/239; 548/237
[58] Field of Search ............................... 548/237, 239

[56] References Cited

U.S. PATENT DOCUMENTS

| | | | |
|---|---|---|---|
| 2,831,858 | 4/1958 | de Benneville et al. | 548/239 |
| 3,562,263 | 2/1971 | Litt | 548/237 |
| 3,639,601 | 1/1972 | Junghahnel et al. | 514/374 |
| 3,681,329 | 8/1972 | Litt | 548/237 |
| 3,681,333 | 8/1972 | Litt | 548/237 |
| 4,479,888 | 10/1984 | Koch | 548/237 |
| 4,705,764 | 10/1987 | Matsumoto | 556/4 |
| 5,034,536 | 7/1991 | Fazio | 548/239 |

FOREIGN PATENT DOCUMENTS

| | | |
|---|---|---|
| 0105944 | 4/1984 | European Pat. Off. . |
| 0164219 | 12/1985 | European Pat. Off. . |
| 0033752 | 4/1987 | European Pat. Off. . |
| 0019661 | 2/1977 | Japan ........................... 541/88 |

OTHER PUBLICATIONS

Chem. Abst. 87:135352h, 2–Oxazolines and 5,6–dihydro–4H–1,3 oxazine, Japan.
Chem. Abst. 87:135353j, 2–Oxazoline and 5,6–dihydro–4H–1,3 oxazine, Japan.
Chem. Rev. 71, 485 ff (1971).

*Primary Examiner*—Donald G. Daus
*Attorney, Agent, or Firm*—Ernest G. Szoke; Wayne C. Jaeschke; Real J. Grandmaison

[57] ABSTRACT

A process for the production of 2-alkyl- or alkenyl-2-oxazolines, in which the alkyl or alkenyl group may be a hydroxy-, dihydroxy- or hydroxy, $C_1$-$C_2$-alkoxy-substituted hydrocarbon radical containing at least 7 carbon atoms, produces the subject compounds in high yields when $C_8$-$C_{22}$ fatty acids or esters thereof are reacted with 2-amino-ethanol or ethanolamides of these fatty acids in the presence of titanium or zirconium compounds corresponding to the formula $M(OR^2)_4$ wherein M=Ti or Zr.

21 Claims, No Drawings

PROCESS FOR THE PRODUCTION OF 2-ALKYL- OR ALKENYL-2-OXAZOLINES

This application is a continuation of application Ser. No. 07/481,744, filed Feb. 14, 1990, now abandoned, which is a continuation of application Ser. No. 07/269,271, filed Nov. 9, 1988, now abandoned.

BACKGROUND OF THE INVENTION

1. Field of the Invention

This invention relates to a process for the production of 2-alkyl- or alkenyl-2-oxazolines corresponding to general formula (I)

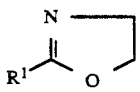
(I)

in which $R^1$ is an optionally hydroxy-, dihydroxy- or hydroxy, $C_1$-$C_2$-alkoxy-substituted hydrocarbon radical containing at least 7 and more especially 7 to 21 carbon atoms in the carbon chain, by condensation of fatty acid ethanolamides or precursors thereof in the presence of catalysts in the liquid phase.

2. Discussion of Related Art

2-Alkyl-substituted 2-oxazolines are valuable intermediate products which are used inter alia as solvents or plasticizers and, in particular, as polymerization components. Numerous processes have been described for the preparation of this class of compounds.

The most simple method comprises the cyclodehydration of N-2-hydroxyethyl carboxylic acid amides (Chem. Rev. 44, 447 et seq. (1949), Chem. Rev. 71, 485 et seq. (1971)). However, cyclization of the unsubstituted N-2-hydroxyethyl carboxylic acid amides requires very drastic conditions or the presence of special catalysts. Whereas reactions in the gas phase in the presence of dehydrating metal oxides, such as $Al_2O_3$, $SiO_2$-$Al_2O_3$, $Al_2O_3$-$TiO_2$, $TiO_2$ or MgO, have proven to be suitable for the production of readily volatile, short-chain 2-alkyl-2-oxazolines, the less volatile, longer-chain 2-alkyl-2-oxazolines are better produced in the liquid phase. Compounds of manganese, cobalt, molybdenum, tungsten, iron, cadmium, zinc and tin and of the rare earth metals have been described as catalysts for the liquid-phase reaction (cf. U.S. Pat. No. 3,562,263, Belgium Patent 666,829, C.A. 87, 135353, C.A. 87, 135352, U.S. Pat. No. 3,681,329, U.S. Pat. No. 3,681,333, European Patent 00 33 752, U.S. Pat. No. 4,543,414, U.S. Pat. No. 4,354,029, U.S. Pat. No. 4,443,611, European Patent 0 105 944 and European Patent 0 164 219). However, the catalysts described in the above cited publications do not lead to good yields in the preparation of relatively long-chain 2-fatty alkyl-2-oxazolines.

It has now been found that special titanium and zirconium compounds are eminently suitable as catalyst in a process of the type mentioned above with yields of up to about 90% of the theoretical, based on the starting compound, being obtainable.

DESCRIPTION OF THE INVENTION

Other than in the operating examples, or where otherwise indicated, all numbers expressing quantities of ingredients or reaction conditions used herein are to be understood as modified in all instances by the term "about".

Accordingly, the invention is directed to a process of the type mentioned herein, in which $C_8$-$C_{22}$ fatty acids or esters thereof with $C_1$-$C_4$ monoalkanols are condensed with 2-aminoethanol or ethanolamides of these fatty acids in the presence of titanium or zirconium compounds corresponding to general formula II $$M(OR^2)_4 \qquad (II)$$

in which M represents tetravalent titanium or zirconium and $R^2$ is an alkyl group containing at least 2 and more especially 2 to 4 carbon atoms, an acyl group containing at least 2, more especially 2 to 10 carbon atoms, a 2-aminoethyleneoxy group or a residue of a beta-diketone in the enol form corresponding to general formula III $$R^3-C=CH_2-CO-R^4 \qquad III$$

in which $R^3$ and $R^4$ are the same or different and represent a radical from the group consisting of $C_1$-$C_4$ alkyl groups and phenyl optionally substituted in the p-position; two of the radicals $R^2$ together may be formed by the double-bonded radical of a difunctional $C_2$-$C_4$ alkanol, or in the presence of titanyl acetylacetonate or in the presence of condensation products of titanium(IV) or zirconium(IV) tetraalkoxylates corresponding to general formula II, in which M and $R^2$ are as defined above, with polyfunctional alkanols, more especially containing 3 to 12 carbon atoms and 2 to 6 hydroxyl groups, the water or alcohol of reaction is removed in the liquid phase and the 2-alkyl- or alkenyl-2-oxazolines thus obtained are isolated.

The process according to the invention may be applied to any fatty acid ethanolamides or precursors thereof (fatty acids or fatty acid esters) which are derived from linear or branched, saturated or unsaturated fatty acids containing at least 8 carbon atoms, more especially 8 to 22 carbon atoms, including hydroxy- and dihydroxy- or hydroxy, $C_1$-$C_2$-alkoxy-substituted derivatives thereof. Accordingly, the starting compounds for the process according to the invention may be derived from fatty acids of natural, for example vegetable, animal or marine-animal origin or synthetic origin (including technical grade mixtures thereof).

Typical representatives of the natural fatty acids mentioned above include caprylic acid, capric acid, myristic acid, palmitic acid, stearic acid, arachic acid, behenic acid, lignoceric acid, lauroleic acid, myristoleic acid, palmitoleic acid, oleic acid, gadoleic acid, erucic acid, ricinoleic acid, linoleic acid, linolenic acid and arachidonic acid. As normal in oleochemistry, it is generally not the pure fatty acids or ethanolamides which are used, but instead technical grade mixtures thereof, of the type obtainable from natural raw materials, for example from lauric oils, coconut oil, palm oil, palm kernel oil, soybean oil, peanut oil, rapeseed oil, olive oil, linseed oil, sunflower oil, castor oil, beef tallow, lard, and fish oil.

Dihydroxy- or hydroxy, $C_1$-$C_2$-alkoxy-substituted representatives of these fatty acids with vicinal substituents may be prepared from unsaturated fatty acids of the type mentioned above by epoxidation and ring opening of the epoxy groups with water and methanol or ethanol, for example from soybean oil.

The synthetic fatty acids obtainable by oxidation of olefins, paraffins, oxoalcohols and Ziegler alcohols are mentioned as typical representatives of synthetic fatty acids suitable for use in the process according to the invention.

The fatty acid ethanolamides suitable for use in the process according to the invention may be obtained by standard methods, for example in accordance with U.S. Pat. No. 4,203,900.

The titanium or zirconium compounds suitable for use as catalysts in the process according to the invention are known and, for the most part, are commercially obtainable. Condensation products of titanium(IV) or zirconium(IV) tetralkoxylates with polyfunctional alkanols containing 3 to 12 carbon atoms and 2 to 6 hydroxyl groups, such as glycerol, trimethylolpropane and pentaerythritol, are esterification and/or transesterification catalysts which are described, for example, in U.S. Pat. No. 4,705,764. Another suitable polyalcohol is polyvinyl alcohol. The titanium or zirconium tetra-(2-aminoethoxylates) are also suitable as catalysts and can be prepared from titanium or zirconium tetralkoxylates and 2-aminoethanol.

In one preferred embodiment of the invention, the catalysts used are esters of titanic acid ($H_4TiO_4$) or zirconic acid ($H_4ZrO_4$) or mixed anhydrides of titanic or zirconic acid with organic acids corresponding to general formula II, in which M=Ti or Zr and $R^2$ is an alkyl group containing at least 2, more especially 2 to 4, carbon atoms or an acyl group derived from a monocarboxylic acid containing 2 or more than 2, more especially 2 to 10, carbon atoms.

In another advantageous embodiment of the invention, catalysts from the group consisting of titanium or zirconium tetraethylate, tetrapropylate, tetraisopropylate, tetrabutylate and tetraacetate are used.

In another advantageous embodiment of the invention, the catalysts used are titanium or zirconium acetylacetonates reacted in the corresponding to general formula (IV)

$$(R^5O)_mM(ACA)_n \qquad (IV)$$

in which $R^5$ is a $C_1$-$C_4$ alkyl group, ACA is an acetylacetonate group and m=0 and n=4, or m=2 and n=2.

In another advantageous embodiment of the invention, polycondensation products of esters of titanic acid with $C_2$-$C_{10}$ monoalkanols with pentaerythritol are used as catalysts.

In another advantageous embodiment of the invention, the catalysts used in accordance with the invention are employed in a quantity of 0.1 to 3 mol-%, preferably in a quantity of 0.5 to 2 mol-%, and more preferably in a quantity of 0.5 to 1 mol-%, based on fatty acid ethanolamide or precursor.

In another advantageous embodiment of the invention, the condensation reaction is carried out at 150° to 270° C., the reaction preferably being carried out in vacuo and in an inert gas atmosphere. The water of reaction formed may be distilled off together with the 2-alkyl- or alkenyl-substituted 2-oxazolines and separated therefrom during distillation, the residual water entrained, particularly in the case of relatively short-chain 2-alkyl- or alkenyl-2-oxazolines, being removed using standard siccatives, such as anhydrous sodium sulfate or molecular sieve (4A). However, the water of reaction may also be removed from the reaction mixture by azeotropic distillation using high-boiling entraining agents, such as for example tetralin or cumene, before the actual distillation of the 2-oxazolines.

In another preferred embodiment of the invention, the 2-alkyl-or alkenyl-substituted 2-oxazolines may be directly prepared from fatty acids or fatty acid esters corresponding to general formula (V)

$$R^1\text{---}COOR^6 \qquad (V)$$

in which $R^1$ is as defined above, and $R^6$ is hydrogen or a $C_1$-$C_4$ alkyl group, by reacting these fatty acids or fatty acid esters with ethanolamine at elevated temperature to form the fatty acid ethanolamides with removal of the alcohol or water of reaction and leaving the reaction mixture to react in a second reaction stage in which the reaction temperature is further increased. In this case, the technical grade readily obtainable fatty acid methyl esters are preferably used as the starting materials. They are reacted in the presence of ethanolamine and the claimed catalysts in a first reaction stage at elevated temperature with removal of alcohol or water of reaction to form fatty acid ethanolamides and the reaction mixture is left to react in a second reaction stage in which the reaction temperature is further increased. The ethanolamine is preferably used in an excess of 50 to 400 mol-%, based on the starting material, unreacted or excess ethanolamine being removed from the reaction mixture before the second reaction stage. A reaction temperature of 100° to 150° C. is preferably employed in the first reaction stage and a reaction temperature of 150° to 250° C. in the second reaction stage. The catalysts are preferably used in a quantity of 0.01 to 3 mol-%, more preferably in a quantity of 0.5 to 2 mol-% and most preferably in a quantity of 0.5 to 1 mol-%, based on the starting material used. The catalysts preferably used are again titanium tetraalcoholates, more especially selected from the group consisting of titanium tetraethylate, propylate, isopropylate and butylate. Alternatively, mixed anhydrides of titanic acid with mono-carboxylic acids, more especially those containing 1 to 4 carbon atoms, preferably titanium tetraacetate, are used. Other preferred catalysts are titanium or zirconium acetylacetonates corresponding to general formula IV and the above mentioned polycondensation products of esters of titanic acid with $C_2$-$C_{10}$ monoalcohols with pentaerythritol and also titanium-(IV) or Zr(IV) tetraaminoethanolates.

In this embodiment of the process, the reaction is again carried our in vacuo and the water of reaction formed is distilled off together with the 2-alkyl- or alkenyl-substituted 2-oxazolines with further separation during distillation or, alternatively, the water of reaction is removed by azeotropic distillation before the distillation of the 2-alkyl- or alkenyl-2-oxazolines as discussed above.

It is of particular advantage here to carry out the first and second stages of the reaction as a one-pot process in one and the same reactor.

The present invention also relates to 2-alkyl- or alkenyl-2-oxazolines corresponding to general formula I, in which $R^1$ is a hydrocarbon radical from the group consisting of 11-hydroxy-8-heptadecenyl and 11-hydroxy-8 or 11-hydroxy-8-heptadecadienyl, as new compounds which may be used as monomers or comonomers in polymerization reactions.

11-Hydroxy-8-heptadecenyl-2-oxazoline may be obtained from ricinoleic acid or esters or diethanolamides thereof by the process according to the invention. It is generally prepared from technical grade castor oil fatty acid which contains smaller fractions of other fatty acids and has the following approximate composition:

$C_{16}$ saturated: 1–2%
$C_{18}$ saturated: 1–2%
$C_{18}$ monounsaturated: traces–8.5%
Ricinoleic acid (12-hydroxyoctadecenoic acid): 86–92%
$C_{18}$ diunsaturated: 3–6%

11,8 (11,9)-Heptadecadienyl-2-oxazoline may be obtained in the same way as described above from ricinene fatty acid which in turn is formed during the elimination of 1 mol of water from ricinoleic acid or technical grade castor oil fatty acid.

11,8-Heptadecadienyl-2-oxazoline may be obtained from linoleic acid or from esters of diethanolamides thereof by the process according to the invention. Once again, it is best not to use a pure linoleic acid, but instead a technical grade fatty acid mixture rich in linoleic acid which may be obtained from vegetable oils, particularly soybean oil, and which typically has the following composition:

$C_{10}$ saturated: 0–0.5%
$C_{12}$ saturated: 0–0.5%
$C_{14}$ saturated: 0–2%
$C_{16}$ saturated: 8–13%
$C_{18}$ saturated: 3–6%
$C_{18}$ monounsaturated: 23–30%
$C_{18}$ diunsaturated: 40–50%
$C_{18}$ triunsaturated: 4–12%
$C_{20}$ monounsaturated)
$C_{22}$ saturated): 0–2%

The invention is illustrated by the following examples.

EXAMPLE 1

Preparation of 2-undecyl-2-oxazoline

A mixture of 546.8 g (2.5 mol) of lauric acid methyl ester (98%), 307 g (5 mol) of ethanolamine and 8.5 g (0.025 mol, 1 mol-%) of titanium tetrabutylate was introduced into a stirred reactor equipped with a fractionating column, a descending condenser with distillation receivers, a vacuum attachment with a cold trap for the water of reaction, a thermometer and a gas inlet pipe for nitrogen as the inert gas.

The methanol formed was distilled off first at normal pressure and then in a weak vacuum (200 hPa) at 120° to 140° C.

The excess ethanolamine was then distilled off in vacuo at 120° C./4 hPa.

The lauric acid ethanolamide thus obtained was heated in vacuo to 180°–250° C., the 2-undecyl-2-oxazoline and water distilling over simultaneously at 180°–210° C./4 hPa. The water of reaction was distilled off through the condenser at the head of the column and condensed in a cold trap. To free the 2-undecyl-2-oxazoline distilled over from any water entrained, a siccative, such as for example sodium sulfate or molecular sieve 4A, was added to the distillation receivers.

2-Undecyl-2-oxazoline still containing small quantities of lauric acid ethanolamide was obtained in a yield of 489 g (87% of the theoretical, based on the fatty acid methyl ester used. $n^{20}$: 1.4670. 447 g (80% of the theoretical) of pure 2-undecyl-2-oxazoline was obtained by another fractional distillation (Bp.: 154°–158° C. at 4 hPa).
$n^{20}$: 1.4562.
Analysis $C_{14}H_{27}NO$ (225.4): $N_{calc.}=6.2$, $N_{found}$ 6.5.

IR: 1671 (C=N); 1230, 1169 (C—O—C=); 989, 954, 906 (oxazoline), 722 (C—H) cm$^{-1}$.

The $^1$H-NMR was in accordance with the structure.

EXAMPLE 2

Preparation of 2-heptadecyl-2-oxazoline

As in Example 1, 597 g (2 mol) of stearic acid methyl ester (94%), 245.5 g (4 mol) of ethanolamine and 4 g (0.012 mol, 0.6 mol-%) of titanium tetrabutylate were reacted under nitrogen and normal pressure at 140°–175° C. to form stearic acid ethanolamine with removal of methanol by distillation. The excess ethanolamine was then distilled off in a water jet pump vacuum (20 hPa) at 115°–200° C. The temperature was then increased in an oil pump vacuum (0.007 hPa) to 220°–300° C., 2-heptadecyl-2-oxazoline and water distilling over.

Crude 2-heptadecyl-2-oxazoline was obtained in a yield of 538 g (87% of the theoretical).

After another vacuum distillation (Bp.: 208° C. at 0.007 hPa), pure 2-heptadecyl-2-oxazoline (Mp.: 51–53) was obtained in a yield of 469 g (76% of the theoretical).
Analysis $C_{20}H_{39}NO$ (309.5): $N_{calc.}=4.5$, $N_{found}=4.6$.
IR: 1667 (C=N); 1234, 1165 (C—O—C=); 989, 957, 916 oxazoline), 718 (C—H) cm$^{-1}$.

The $^1$H-NMR was in accordance with the structure.

EXAMPLE 3

Preparation of 2-(8-heptadecen-1-yl)-2-oxazoline

As in Example 1, 445.7 g (1.5 mol) of technical grade oleic acid methyl ester (sunflower oil fatty acid, oleic acid content approx. 85%, saponification value 188.8, iodine value 85), 184.2 g (3 mol) of ethanolamine and 5.1 g (0.015 mol, 1 mol-%) of titanium tetrabutylate were reacted under nitrogen and normal pressure at 140° to 150° C. to form oleic acid ethanolamide with removal of methanol by distillation. The excess ethanolamine was then distilled off at 4 hPa/120°–125° C. The temperature was then increased to 220°–265° C. at 0.08–0.1 hPa, the product and water distilling over. 2-(8-Heptadecen-1-yl)-2-oxazoline was obtained in a yield of 394.1 g (86% of the theoretical). $n^{20}$: 1.4700.

IR: 1671 (C=N); 1230, 1173 (C—O—C=); 989, 953, 916 (oxazoline); 772 (C—H).

EXAMPLE 4

Preparation of an 2-fatty alkenyl-2-oxazoline from soybean oil fatty acid methyl ester Following the procedure of Example 1, soybean oil fatty acid methyl ester was reacted with ethanolamine to form 2-fatty alkenyl-2-oxazoline. The quantities used were as follows:
433.8 g (1.5 mol) of soybean oil fatty acid methyl ester (saponification value 194, molecular weight 289.2, iodine value 124);
184.2 g (3 mol) of ethanolamine;
5.1 g (0.015 mol, 1 mol-%) of titanium tetrabutylate.

Yield: 374 g (83% of the theoretical) of 2-fatty alkenyl-2-oxazoline. Bp: 187° C. (0.13 hPa). $n^{20}$: 1.4746.

IR: 1671 (C=N); 1231, 1172 (C—O—C=); 989, 953, 916 (oxazoline); 723 (C—H) cm$^{-1}$.

EXAMPLE 5

Preparation of 2-undecyl-2-oxazoline

Following the procedure of Example 1, lauric acid methyl ester was reacted with ethanolamine in the presence of titanium tetraacetate to form 2-undecyl-2-oxazoline. The quantities used were as follows:
107.3 g (0.5 mol) of lauric acid methyl ester;
61.4 g (1 mol) of ethanolamine; and
0.85 g (0.002 mol, 0.6 mol-%) of titanium tetraacetate.
Yield: 97.8 g (84% of the theoretical) of 2-undecyl-2-oxazoline. Bp: 162° C. (17 hPa). $n^{20}$: 1.4570 (corresponds to the product of Example 1).

EXAMPLE 6

Preparation of an 2-fatty alkenyl-2-oxazoline from soybean oil fatty acid methyl ester A mixture of 52.8 kg (180 mol) of soybean oil fatty acid methyl ester (saponification value 194, molecular weight 289.2, iodine value 120), 22.2 kg (360 mol) of ethanolamine and 0.62 kg (1.8 mol, 1 mol-%) of titanium tetrabutylate was introduced into a stirred reactor of stainless steel equipped with a heatable ascending condenser in the form of a column, a descending condenser with distillation receivers, a vacuum attachment with a cold trap for the water of reaction, a thermometer and a gas inlet pipe for nitrogen as the inert gas.

The methanol formed was distilled off in a stream of nitrogen over a period of several hours at 120° to 180° C. The excess ethanolamine was then distilled off in vacuo at 120° to 180° C./24 hPa. The soybean oil fatty acid ethanolamine thus obtained was heated in vacuo to 160°–230° C., the 2-soyaalkenyl-2-oxazoline and the water of reaction distilling over at 180°–210° C./2 hPa through the condenser heated to 200° C.

2-Soyaalkenyl-2-oxazoline was obtained in a yield of 48.6 kg (90% of theoretical, based on the soybean oil fatty acid methyl ester used).

EXAMPLE 7

Preparation of 2-ricinolalkenyl-2-oxazoline (2-(11-hydroxyheptadec-8-en-1-yl-2-oxazoline))

Following the procedure of Example 1, ricinoleic acid methyl ester was reacted with ethanolamine to form 2-ricinolalkenyl-2-oxazoline. The quantities used were as follows:
383.4 g (125 mol) of castor oil methyl ester (saponification value 183; molecular weight 306.7; iodine value 76, OH value 14.5);
153.5 g (2.5 mol) of ethanolamine; and
4.25 g (0.0125 mol, 1 mol-%) of titanium tetrabutylate.
Yield: 278 g (70% of the theoretical) of 2-ricinolalkenyl-2-oxazoline. Bp: 200° C. at 0.027 hPa. $N^{20}$: 1.478.

Analysis:
IR: 3334 (OH); 1667 (C=N); 1240, 1179 (C—O—C=) 991, 958, 916 (oxazoline) 726 (C—H) cm$^{-1}$ $C_{20}H_{27}NO_2$ (325, 524); $C_{calc.}$=74.25; $C_{found}$=74.4; $H_{calc.}$=11.53; $H_{found}$=11.55; $N_{calc.}$=4.33; $N_{found}$=4.79.
Iodine value$_{calc.}$=76.4, Iodine value$_{found}$=80.7

EXAMPLE 8

2-Undecyl-2-oxazoline from lauric acid methyl ester using zirconium tetrabutylate as catalyst Following the procedure described in Example 2, lauric acid methyl ester was reacted with ethanolamine in the presence of zirconium tetrabutylate as catalyst to form the title compound. The quantities used were as follows: 273.0 g (1.25 mol) of lauric acid methyl ester (98.6%), 153.5 g (2.5 mol of ethanolamine, and 4.8 g (0.0125 mol) of zirconium tetrabutylate. Yield: 248.6 g (87.7% of the theoretical). $n^{20}$: 1.4565.

EXAMPLE 9

Preparation of 2-undecyl-2-oxazoline from lauric acid methyl ester using zirconium (IV) acetylacetonate Following the procedure described in Example 2, lauric acid methyl ester was reacted with ethanolamine in the presence of zirconium (IV) acetylacetonate to form the title compound. The quantities used were as follows:
273.4 g (1.25 mol) of lauric acid methyl ester (98.6%);
153.5 g (2.5 mol) of ethanolamine; and
6.1 g (0.0125 mol) of zirconium (IV) acetylacetonate.
Yield: 226.2 g (80% of the theoretical). $n_D^{20}$: 1.4562.

EXAMPLE 10

2-Pentadecyl-2-oxazoline from palmitic acid using titanium tetrabutylate as catalyst Following the procedure described in Example 2, palmitic acid was reacted with ethanolamine in the presence of titanium tetrabutylate to form 2-pentadecyl-2-oxazoline. The quantities used were as follows:
392.5 g (1.5 mol) of palmitic acid (98%);
184.2 g (3.0 mol) of ethanolamine (99.5%); and
5.1 g (0.015 mol) of titanium tetrabutylate.
Yield: 342.2 g (81% of the theoretical). Bp (0.3 torr; 0.41 hPa): 178° C. Mp.: 47° C.
Analysis $C_{18}H_{36}NO$ (282.5): C=76.9 (theoretical 76.5), H-12.3 (theoretical 12.8), N=5.05 (theoretical 5.0).
The IR spectrum was in accordance with the structure given for the title compound.

EXAMPLE 11

2-ricinolalkenyl-2-oxazoline
2-(11-hydroxyheptadec-8-en-1-yl)-2-oxazoline)

Following the procedure described in Example 2, a technical grade ricinoleic acid methyl ester (saponification value 182.9, iodine value 76.4, OH value 142.5) was reacted with ethanolamine in the presence of titanium tetrabutylate as catalyst to form 2-ricinolalkenyl-2-oxazoline. The quantities used were as follows:
383.4 g (1.25 mol) of ricinoleic acid methyl ester (MW=306.7);
153.5 g (2.5 mol) of ethanolamine (99.5%); and
4.25 g (0.0125 mol) of titanium tetrabutylate.
Yield: 306.4 g (77.,4% of the theoretical). Bp. (0.3 torr; 0.4 hPa): 220° C. $n^{20}$: 1.4788.
Analysis $C_{20}H_{37}NO_2$ (323.52): C=74.4 (theoretical 74.25), H=11.55 (theoretical 11.53), N=4.50 (theoretical 4.33), iodine value=79.7 (theoretical 78.6).
The IR and $^1$HMR spectra were in accordance with the structure given for the title compound.

EXAMPLE 12

Preparation of 2-heneicosyl-2-oxazoline from behenic acid and ethanolamine using titanium tetrabutylate as catalyst Following the procedure of Example 2, behenic acid was reacted with ethanolamine in the presence of titanium tetrabutylate as catalyst to form 2-heneicosyl-2-oxazoline.

Since heneicosyl-2-oxazoline tends to sublimate, two distillation receivers were used. The first distillation receiver was heated with stirring to 80° C. while the second distillation receiver was cooled with liquid nitrogen to collect all the water of reaction.

The quantities used were as follows:
709.3 g (2.085 mol) of behenic acid (acid value 165);
254.8 g (4.17 mol of ethanolamine; and
7.14 g (0.021 mol) of titanium tetrabutylate.

Yield: 662 g (87% of the theoretical). Bp$_{0.15}$hPa: 172° C.

Mp.: 54°-55° C.

IR: $v=1668$ (C=N); 1236, 1164 (C—O—C=); 991, 956, 915 (oxazoline); 717 (C—H)cm$^{-1}$.

EXAMPLE 13

Preparation of 2-(12-heneicosenyl)-2-oxazoline from erucic acid and ethanolamine using titanium tetrabutylate as catalyst Following the procedure of Example 10, erucic acid was reacted with ethanolamine in the presence of titanium tetrabutylate as catalyst to form 2-(12-heneicosenyl)-2-oxazoline. The quantities used were as follows:

751.6 g (2.28 mol) of erucic acid (acid value 170);
277.9 g (4.55 mol) of ethanolamine; and
7.7 g (0.021 mol) titanium tetrabutylate.

Yield: 649.6 g (80% of the theoretical). Bp$_{0.15}$hPa: 162° C. n$_D^{20}$: 1.4710.

IR: $v=1671$ (C=N); 1237, 1170 (C—O—C=); 988, 952, 906 (oxazoline) 721 (C—H) cm$^{-1}$

EXAMPLE 14

Preparation of 2-isoheptadecyl-2-oxazoline from isostearic acid and ethanolamine using titanium tetrabutylate as catalyst The quantities used were as follows:
884.7 g (3 mol) of isostearic acid (acid value 190);
366.5 g (6 mol) of ethanolamine; and
10.2 g (0.03 mol) of titanium tetrabutylate.

Yield: 739.1 g (77% of the theoretical). Bp$_{0.15}$hPa: 132°-137° C. n$_D^{20}$: 1.4670.

IR: $v=1671$ (C=N); 1229, 1170 (C—O—C=); 988, 953, 916 (oxazoline) 725 (C—H).

EXAMPLE 15

Preparation of 2-(hydroxymethoxyheptadecyl)-2-oxazoline from hydroxymethoxystearic acid methyl ester and ethanolamine using titanium tetrabutylate as catalyst Following the procedure of Example 2, hydroxymethoxystearic acid was reacted with ethanolamine to form 2-(hydroxymethoxyheptadecyl)-2-oxazoline.

The quantities used were as follows:
504.8 g (1.5 mol) of hydroxymethoxystearic acid methyl ester (saponification value 167, OH value 145, iodine value 4.7);
184.2 g (0.3 mol) of ethanolamine; and
5.1 g (0.015 mol) of titanium tetrabutylate.

Yield: 284.6 g (55% of the theoretical) (main fraction). Bp$_{0.08}$hPa: 230°-240° C. n$_D^{20}$: 1.4702.

IR: $v=3326$ (—OH); 1668 (C=N); 1234, 1171 (C—O—C=) 990, 956, 916, (oxazoline) 723 (C—H) iodine value: 7.6

EXAMPLE 16

Preparation of 2-undecyl-2-oxazoline from lauric acid methyl ester and ethanolamine using pentaerythritol polytitanate as catalyst:

The quantities used were as follows;
273.4 g (125 mol) of lauric acid methyl ester,
153.5 g (2.5 mol) of ethanolamine, and
3.1 g (0.0125 mol) pentaerythritol polytitanante (according to U.S. Pat. No. 4,705,764)

Yield: 264 g (94% of the theoretical) 248.2 g (main fraction) (88% of the theoretical) secondary fraction 8.4 g; acid value 6.0.

The reaction time for the formation of the oxazoline from the ethanolamine was 1.5 hours.

The catalyst could be filtered off from ethanolic solution and showed no loss of activity after it had been used three times.

EXAMPLE 17

Preparation of 2-undecyl-2-oxazoline using tetra-(aminoethyl) titanate

A mixture of 98.2 g (1.6 mol) of ethanolamine and 68.1 g (0.2 mol) of titanium tetrabutylate was heated in a stream of nitrogen for 3 hours to 150° C. in a stirred reactor equipped with a distillation column, 60.8 g distilling off; this corresponds to a complete conversion (theoretical: 59.3 g). The residue weighted 103 g and consisted of an approximately 56% yellowish solution of tetra(aminoethyl) titanate in ethanolamine which was used as the catalyst solution.

2-Undecyl-2-oxazoline

A mixture of 546.8 g (2.5 mol) of lauric acid methyl ester (98%), 307 g (5 mol) of ethanolamine (95.5%) and 25.8 g (0.05 mol) (2 mol-%) of tetra(aminoethyl) titanate (56%) was introduced into a stirred reactor equipped with a fractionating column, a descending condenser and distillation receivers, a vacuum attachment with a cold trap for the water of reaction, a thermometer and a gas inlet pipe for nitrogen as the inert gas. At 140° to 170° C., the methanol formed was distilled off at normal pressure, the remaining methanol then being distilled off in a slight vacuum (200 hPa).

The excess ethanolamine was then distilled off in vacuo at 95°-180° C./18-3 hPa. The lauric acid ethanolamine obtained was heated in vacuo to 180°-200° (230°)°C., the title compound distilling over at 140°-160° C./2.7 hPa. The water of reaction was almost completely condensed in the cold trap.

The title compound was obtained in a yield of 484.5 g (86% of the theoretical, based on the fatty acid methyl ester used), some fractions still containing small quantities of lauric acid ethanolamine. 445.3 g (80% of the theoretical) of the title compound were obtained as the pure fraction. n$_D^{20}$: 1.4562. Bp. (2.7 hPa): 144° C.

EXAMPLE 18

Preparation of 2-undecyl-2-oxazoline from lauric acid using tetra(aminoethyl) titanate Following the procedure of Example 17, lauric acid was reacted with ethanolamine in the presence of tetra(amino-ethyl) titanate as catalyst to form the title compound. The quantities used were as followed:
505.8 g (2.5 mol) of lauric acid (99%);
307 g (5 mol) of ethanolamine (99.5%); and 12.9 g (0.025 mol) of tetra(aminoethyl) titanate.

Yield: 481.3 g (85% of the theoretical) of 2-undecyl-2-oxazoline. $n_D^{20}$: 1.4565.

EXAMPLE 19

Preparation of 2-undecyl-2-oxazoline from lauric acid using tetrabutyl titanate as catalyst Following the procedure described in Example 17, lauric acid was reacted with ethanolamine in the presence of tetrabutyl titanate as catalyst to form the title compound. The quantities used were as follows:
252.9 g (1.25 mol) of lauric acid (99%);
153.5 g (2.5 mol) of ethanolamine; and
4.25 g (0.0125 mol) of tetrabutyl titanate.

Yield: 244.2 g (87% of theoretical) of 2-undecyl-2-oxazoline. $n_D^{20}$: 1.4565.

When the catalyst was reused, substantially the same yield was obtained.

EXAMPLE 20

Preparation of 2-undecyl-2-oxazoline from lauric acid methyl ester using titanium(IV) acetylacetonate Following the procedure of Example 17, lauric acid methyl ester was reacted with ethanolamine in the presence of titanium(IV) acetylacetonate to form the title compound. The quantities used were as follows:
273.4 g (1.25 mol) of lauric acid methyl ester;
153.5 g (2.5 mol) of ethanolamine; and
3.3 g (0.125 mol) of titanium(IV) acetylacetonate.

Yield: 257.3 g (91% of theoretical) 241.8 g (86% of theoretical) pure fraction.
$n_D^{20}$: 1.4565.

We claim:

1. A process for the production of 2-alkyl-or alkenyl-2-oxazolines corresponding to formula I

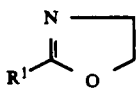 (I)

in which $R^1$ is a hydroxy-, dihydroxy- or hydroxy, $C_1$-$C_2$-alkoxy-substituted hydrocarbon radical having 7 to 21 carbon atoms in the carbon chain, comprising condensing in the liquid phase a $C_8$-$C_{22}$ fatty acid or ester thereof with a $C_1$-$C_4$ monoalkanol and 2- aminoethanol or an ethanolamide of said fatty acid in the presence of a titanium or zirconium catalyst, said catalyst being selected from the group consisting of (1) a titanium or zirconium compound corresponding to formula II $(M(OR^2)_4$  (II)

in which M represents tetravalent titanium or zirconium, and $R^2$ is an acyl group having 2 to 10 carbon atoms, a 2-aminoethyleneoxy group, or a residue of a beta-diketone in the enol form corresponding to formula III $R^3$—C=CH$_2$—CO—$R^4$ (III)

wherein $R^3$ and $R^4$ are the same or different and represent a radical consisting of a $C_1$-$C_4$ alkyl group, (2) titanyl acetylacetonate, and (3) a condensation product of titanium (IV) or zirconium (IV) tetraalkoxylate corresponding to formula II, in which M and $R^2$ are as defined above, with a polyfunctional alkanol having 3 to 12 carbon atoms and 2 to 6 hydroxy groups, removing the alcohol or water of reaction formed, and isolating the 2-alkyl- or 2-alkenyl-2-oxazoline obtained.

2. A process as in claim 1 wherein said catalyst comprises tetra(aminoethyl) titanate or zirconate.

3. A process as in claim 1 herein said catalyst comprises a titanium acetylacetonate corresponding to formula IV $(R^5O)_mM(ACA)_n$  (IV)

in which $R^5$ is a $C_1$-$C_4$ alkyl group, ACA is an acetylacetonate group and m=0 and n=4, or m=2 and n=2.

4. A process as in claim 1 wherein said catalyst comprises a polycondensation product of an ester of titanic acid with a $C_2$-$C_{10}$ monoalkanol and pentaerythritol.

5. A process as in claim 1 wherein said catalyst is used in a quantity of from about 0.1 to about 3 mol-%, based on said fatty acid ethanolamide.

6. A process as in claim 1 wherein said condensing step is carried out at about 150° to about 270° C.

7. A process as in claim 1 carried out in vacuo.

8. A process as in claim 1 wherein the alcohol or water of reaction formed is distilled off together with the 2-alkyl- or alkenyl-substituted 2-oxazolines and is separated therefrom either subsequently or at the same time or is removed by azeotropic distillation before the distillation of said oxazolines.

9. A process as in claim 1 wherein in a first reaction stage, a fatty acid or fatty acid ester corresponding to formula V $R^1$—COOR$^6$  (V)

in which $R^1$ is as defined above and $R^6$ is hydrogen or a $C_1$-$C_4$ alkyl group, is reacted with ethanolamine at elevated temperature to form the fatty acid ethanolamide with removal of the alcohol or water of reaction and the reaction mixture is left to react in a second reaction stage in which the reaction temperature is further increased.

10. A process as in claim 9 wherein said ethanolamine is present in an excess of about 50 to about 400 mol-%, based on the fatty acid ester used.

11. A process as in claim 9 wherein unreacted or excess ethanolamine is removed from the reaction mixture before the second reaction stage.

12. A process as in claim 9 wherein a reaction temperature of about 100° to about 150° C. is used in the first reaction stage.

13. A process as in claim 9 wherein a reaction temperature of about 150° to about 270° C. is used in the second reaction stage.

14. A process as in claim 9 wherein said catalyst comprises a tetra(aminoethyl) titanate or zirconate.

15. A process as in claim 9 wherein said catalyst comprises a mixed anhydride of titanic acid with a monocarboxylic acid.

16. A process as in claim 9 wherein said catalyst comprises a titanium acetylacetonate corresponding to formula IV $(R^5O)_m(M(ACA)_n$  (IV)

in which $R^5$, ACA, m and n are as defined in claim 3.

17. A process as in claim 9 wherein said catalyst comprises a polycondensation product of an ester of titanic acid with a $C_2$-$C_{10}$ monoalkanol and pentaerythritol.

18. A process as in claim 9 wherein said catalyst is present in a quantity of 0.01 to 3 mol-%, based on said fatty acid or fatty acid ester.

19. A process as in claim 9 carried out in vacuo.

20. A process as in claim 9 wherein the alcohol or water of reaction formed in the second reaction stage is distilled off together with the 2-alkyl- or simultaneously removed or is removed by azeotropic distillation before the distillation of 2-oxazolines.

21. A process as in claim 9 wherein the first and second stages of the reaction are carried out as a one-pot process.

* * * * *